US009826894B2

(12) United States Patent
Masaki et al.

(10) Patent No.: US 9,826,894 B2
(45) Date of Patent: Nov. 28, 2017

(54) ENDOSCOPE SYSTEM WITH FRAME-SEQUENTIAL LIGHT EMISSION

(71) Applicant: OLYMPUS CORPORATION, Tokyo (JP)

(72) Inventors: Takahiro Masaki, Kawasaki (JP); Yusuke Yabe, Chofu (JP); Tomoya Takahashi, Hachioji (JP); Masato Toda, Hachioji (JP); Yutaka Shirota, Kawasaki (JP); Daisuke Akiyama, Fuchu (JP); Koji Omori, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/011,882

(22) Filed: Feb. 1, 2016

(65) Prior Publication Data

US 2016/0143520 A1      May 26, 2016

Related U.S. Application Data

(63) Continuation of application No. PCT/JP2014/069806, filed on Jul. 28, 2014.

(30) Foreign Application Priority Data

Aug. 1, 2013    (JP) .................................. 2013-160749

(51) Int. Cl.
*A61B 1/04*        (2006.01)
*A61B 1/06*        (2006.01)
(Continued)

(52) U.S. Cl.
CPC ........ *A61B 1/0684* (2013.01); *A61B 1/00009* (2013.01); *A61B 1/04* (2013.01);
(Continued)

(58) Field of Classification Search
CPC ..... A61B 1/00009; A61B 1/0005; A61B 1/04; A61B 1/043; A61B 1/045; A61B 1/05;
(Continued)

(56) References Cited

U.S. PATENT DOCUMENTS

| 2004/0122291 | A1 | 6/2004 | Takahashi |
| 2009/0080175 | A1 | 3/2009 | Mizuno et al. |
| 2012/0271128 | A1* | 10/2012 | Kubo ................. A61B 1/00006 600/317 |

FOREIGN PATENT DOCUMENTS

| EP | 1 079 255 A2 | 2/2001 |
| EP | 1864606 A1 | 12/2007 |

(Continued)

OTHER PUBLICATIONS

Extended Supplementary European Search Report dated Mar. 24, 2017 in European Patent Application No. 14 83 1416.4.
International Search Report dated Aug. 19, 2014 issued in PCT/JP2014/069806.
(Continued)

*Primary Examiner* — Anhtuan T Nguyen
*Assistant Examiner* — William Chou
(74) *Attorney, Agent, or Firm* — Scully, Scott, Murphy & Presser, P.C.

(57) ABSTRACT

An endoscope system including a control section that controls an LED driving section to supply driving currents to LEDs of a plurality of colors to cause the LEDs to emit lights in a frame-sequential manner and a processor that divides a total exposure period in one frame period of the frame-sequential light emission into ratios of light emission periods for each of the respective colors obtained by dividing light amount ratios of the lights of the plurality of colors, which should be received in a CCD, respectively by respective maximum light emission intensities of the LEDs of the plurality of colors and sets respective maximum light emission periods of the LEDs of the plurality of colors.

3 Claims, 10 Drawing Sheets

(51) Int. Cl.
*G02B 23/24* (2006.01)
*A61B 1/00* (2006.01)
*G02B 27/10* (2006.01)

(52) U.S. Cl.
CPC .......... *A61B 1/0638* (2013.01); *A61B 1/0669* (2013.01); *G02B 23/2461* (2013.01); *G02B 27/1006* (2013.01)

(58) Field of Classification Search
CPC ....... A61B 1/06; A61B 1/0638; A61B 1/0661; A61B 1/0669; A61B 1/0684; G02B 23/2461; G02B 23/2484; H04N 5/3532; G03B 9/08
USPC ....... 600/109, 160, 178, 179, 180, 181, 317; 348/45, 65, 69, 70, 294, 340
See application file for complete search history.

(56) References Cited

FOREIGN PATENT DOCUMENTS

| | | |
|---|---|---|
| EP | 2 449 951 A1 | 5/2012 |
| JP | 2003-093336 A | 4/2003 |
| JP | 2006-280465 A | 10/2006 |
| JP | 2010-158415 A | 7/2010 |
| JP | 2011-036361 A | 2/2011 |
| JP | 2012-035090 A | 2/2012 |
| WO | WO 2006/106853 A1 | 10/2006 |
| WO | 2011/079148 A1 | 6/2011 |

OTHER PUBLICATIONS

Japanese Office Action dated Apr. 28, 2015 issued in JP 2015-506436.

* cited by examiner

FIG. 6

| Ig | Sg | Ir | CBr×Sg | Sr | Ib | CBb×Sg | Sb |
|---|---|---|---|---|---|---|---|
| 10 | 100 | 10 | | 60 | 10 | | 120 |
| — | — | — | | — | 10.83 | 100×1.3 =130 | 130 |
| 11 | 110 | 11 | | 66 | 11 | | 132 |
| 12 | 120 | 12 | | 72 | 12 | | 144 |
| 13 | 130 | 13 | | 78 | 13 | | 156 |
| — | — | 13.33 | 100×0.8 =80 | 80 | — | | — |
| . | . | 14 | | 84 | . | | . |
| . | . | . | | . | . | | . |
| . | . | . | | . | . | | . |
| 20 | 200 | 20 | | 120 | 20 | | 240 |

ENDOSCOPE SYSTEM WITH FRAME-SEQUENTIAL LIGHT EMISSION

CROSS REFERENCE TO RELATED APPLICATION

This application is a continuation application of PCT/JP2014/069806 filed on Jul. 28, 2014 and claims benefit of Japanese Application No. 2013-160749 filed in Japan on Aug. 1, 2013, the entire contents of which are incorporated herein by this reference.

BACKGROUND OF THE INVENTION

1. Field of the Invention

The present invention relates to an endoscope system including a light source device that supplies driving currents to light emitting elements having a plurality of colors and causes the light emitting elements to emit lights.

2. Description of the Related Art

As a light source device for illumination light to be radiated from an endoscope to a subject, a xenon lamp or the like has been used conventionally. However, according to spread of LEDs, a light source device including light emitting elements such as LEDs has been put to practical use taking into account low power consumption and durability.

When white light is formed using LEDs, three colors produced by a red LED, a green LED, and a blue LED are enough for forming the white light. However, to also enable narrowband light observation (narrow band imaging: NBI (registered trademark)) that can highlight and observe a blood vessel, a configuration further including a violet LED (V-LED) has been proposed. In the configuration including the violet LED, operation is performed to cause both of the blue LED and the violet LED emit light for blue among red, green, and blue, which are three primary colors forming white light, and give a margin to light intensity of blue light.

A light source device (a frame-sequential system) having such a configuration including the red LED (R-LED), the green LED (G-LED), the blue LED (B-LED), and the violet LED (V-LED) as the light emitting elements is specifically configured, for example, as shown in FIG. 1 related to the present invention.

FIG. 10 is a timing chart of conventional LED lighting control at a time when normal observation is performed with a maximum light amount. FIG. 11 is a diagram showing spectra at a time when the conventional LED lighting control shown in FIG. 10 is performed.

One frame is equally divided into three fields. One field is divided into an exposure period and a readout period. When a light amount is maximized, an LED corresponding to the field is lit at all points in time during the exposure period. Pulse width modulation (PWM) is not performed. At this point, a maximum rated current Igmax is supplied to the green LED as an electric current (see FIG. 10). The red LED, the blue LED, and the violet LED are respectively set to current values for enabling a color balance with respect to an emitted light amount of the green LED. That is, current values less than maximum rated currents Irmax, Ibmax, and Ivmax are supplied to the LEDs of the other colors having higher light emission efficiency than the green LED. An example in which relative light emission intensities of lights emitted from the respective color LEDs are shown as spectra is FIG. 11.

Light emission luminance (brightness) in such a light source device can be adjusted by, for example, increasing or reducing driving current values supplied to the LEDs of the respective colors or performing the pulse width modulation described above.

Concerning color balance adjustment of a light source device, for example, in paragraph [0084] of Japanese Patent Application Laid-Open Publication No. 2011-36361, it is mentioned that, as a method of changing a color tone without changing emitted light amounts of respective light sources, the respective light sources are individually lit and exposure times of an image pickup device 21 at respective lighting timings are changed to simulatively change a color tone of illumination light. More specifically, the respective light sources and the image pickup device are simultaneously controlled, respective exposure times, i.e., an exposure time of the image pickup device for lighting only a first light source such as a blue laser light source to pick up an image and an exposure time for lighting only a second light source such as a white light source are respectively individually increased or reduced to be adjusted, and obtained respective picked-up images are combined as observed image data. Therefore, the color tone change in the publication is considered to be performed by a so-called element shutter.

Further, as a technique for changing brightness while keeping a color balance, for example, in paragraphs [0020], [0025], and [0027] and FIG. 2 of Japanese Patent Application Laid-Open Publication No. 2010-158415, it is mentioned that a light source section 22 includes a first LED 22a for red light emission, a second LED 22b for green light emission, and a third LED 22c for blue light emission and adjustment of driving amounts (e.g., current values in a case of current driving or duty ratios in a case of pulse driving) of first to third LEDs 22a to 22c is performed by a light receiving section 26 that measures emitted light amounts of the first to third LEDs 22a to 22c and an LED driver 21 and that a reference-voltage changing section 21a calculates first to third reference voltage values V1 to V3 according to an instruction signal related to an emitted light amount setting value set by a user such that a ratio of intensities of red emitted by the first LED 22a, green emitted by the second LED 22b, and blue emitted by the third LED 22c is fixed.

On the other hand, concerning adjustment of a light source device involved in aged deterioration of LEDs, for example, in paragraph [0050] of Japanese Patent Application Laid-Open Publication No. 2010-158415 described above, it is mentioned that lights from the first to third LEDs 22a to 22c are received by the light receiving section 26 to acquire information concerning the emitted light amount and the driving amounts and the emitted light amounts of the first to third LEDs 22a to 22c are accurately adjusted taking into account fluctuation in the emitted light amounts due to the aged deterioration, a temperature change, and the like.

SUMMARY OF THE INVENTION

An endoscope system according to an aspect of the present invention includes: light emitting elements of a plurality of colors that generate lights of the plurality of colors to be radiated on a subject; a light-emitting-element driving section that supplies driving currents to the light emitting elements of the plurality of colors and causes the light emitting elements to emit lights; a control section that controls driving of the light-emitting-element driving section to cause the light emitting elements of the plurality of colors to emit lights in a frame-sequential manner according to an input signal; and a processor that divides a total exposure period in the one frame period of the frame-sequential light emission into ratios of light emission periods for each of the respective colors obtained by dividing light amount ratios of the lights of the plurality of colors corresponding to ratios of light amounts which should be received in an image pickup device that generates an image pickup signal of the subject, respectively, by respective maximum light emission intensities obtained when light emission intensities of the light emitting elements of the plurality of colors are maximized and sets respective maximum light emission periods of the light emitting elements of the plurality of colors in one frame period of frame-sequential light emission.

An endoscope system according to an aspect of the present invention includes: light emitting elements of a plurality of colors that generate lights of the plurality of colors to be radiated on a subject; a light-emitting-element driving section that supplies driving currents to the light emitting elements of the plurality of colors and causes the light emitting elements to emit lights; a control section that controls driving of the light-emitting-element driving section to cause the light emitting elements of the plurality of colors to emit lights in a frame-sequential manner according to an input signal; an output section that outputs a timing signal representing end timings of light emission periods of the respective light emitting elements; and a processor that sets respective maximum light emission periods of the light emitting elements of the plurality of colors in one frame period of the frame-sequential light emission based on respective maximum light emission intensities obtained when light emission intensities of the light emitting elements of the plurality of colors are maximized and light amount ratios of the lights of the plurality of colors corresponding to ratios of light amounts which should be received in an image pickup device that generates an image pickup signal of the subject, and further performs control for immediately reading out the image pickup signal from the image pickup device when the timing signals outputted from the output sections are inputted and the light emission periods end on the basis of the timing signals.

An endoscope system according to an aspect of the present invention includes: a light source device including light emitting elements of a plurality of colors that generate lights of the plurality of colors to be radiated on a subject, a light-emitting-element driving section that supplies driving currents to the light emitting elements of the plurality of colors and causes the light emitting elements to emit lights, and a control section that controls driving of the light-emitting-element driving section to cause the light emitting elements of the plurality of colors to emit lights in a frame-sequential manner according to an input signal; a light-emission-intensity detecting section that detects light emission intensities of the light emitting elements of the plurality of colors; a lookup-table storing section that stores a lookup table indicating a relation between the driving currents supplied to the light emitting elements of the plurality of colors and intensities of lights emitted from the light emitting elements to which the driving currents are supplied; and a processor that sets respective maximum light emission periods of the light emitting elements of the plurality of colors in one frame period of the frame-sequential light emission based on respective maximum light emission intensities obtained when light emission intensities of the light emitting elements of the plurality of colors are maximized and light amount ratios of the lights of the plurality of colors corresponding to ratios of light amounts which should be received in an image pickup device that generates an image pickup signal of the subject, and further calculates a brightness value on the basis of the image pickup signal generated by the image pickup device. The light source device performs light adjustment for setting driving currents of the light emitting elements of the plurality of colors on the basis of color balance values indicating light amount ratios of the lights of the plurality of colors, a target brightness value, the brightness value calculated by the processor, and the lookup table such that the brightness value reaches the target brightness value and light amount ratios of the lights of the plurality of colors are light amount ratios indicated by the color balance values.

An endoscope system according to an aspect of the present invention includes: light emitting elements of a plurality of colors that generate lights of the plurality of colors to be radiated on a subject; a light-emitting-element driving section that supplies driving currents to the light emitting elements of the plurality of colors and causes the light emitting elements to emit lights; a control section that controls driving of the light-emitting-element driving section to cause the light emitting elements of the plurality of colors to emit lights in a frame-sequential manner according to an input signal and perform automatic light adjustment according to pulse width modulation control; an image pickup device that picks up an optical image of the subject and is capable of driving an element shutter; and a processor that sets respective maximum light emission periods of the light emitting elements of the plurality of colors in one frame period of the frame-sequential light emission based on respective maximum light emission intensities obtained when light emission intensities of the light emitting elements of the plurality of colors are maximized and light amount ratios of the lights of the plurality of colors corresponding to ratios of light amounts which should be received in the image pickup device that generates an image pickup signal of the subject, and further controls the element shutter and reduces an exposure amount when any one of light emission periods of the light emitting elements of the plurality of colors is a minimum light emission period in the pulse width modulation control and when brightness needs to be further reduced.

BRIEF DESCRIPTION OF THE DRAWINGS

FIG. 6 is a diagram showing an example of a lookup table stored in an LUT storing section in the second embodiment;

DETAILED DESCRIPTION OF THE PREFERRED EMBODIMENTS

Embodiments of the present invention are explained below with reference to the drawings.

[First Embodiment]

Figure 1:
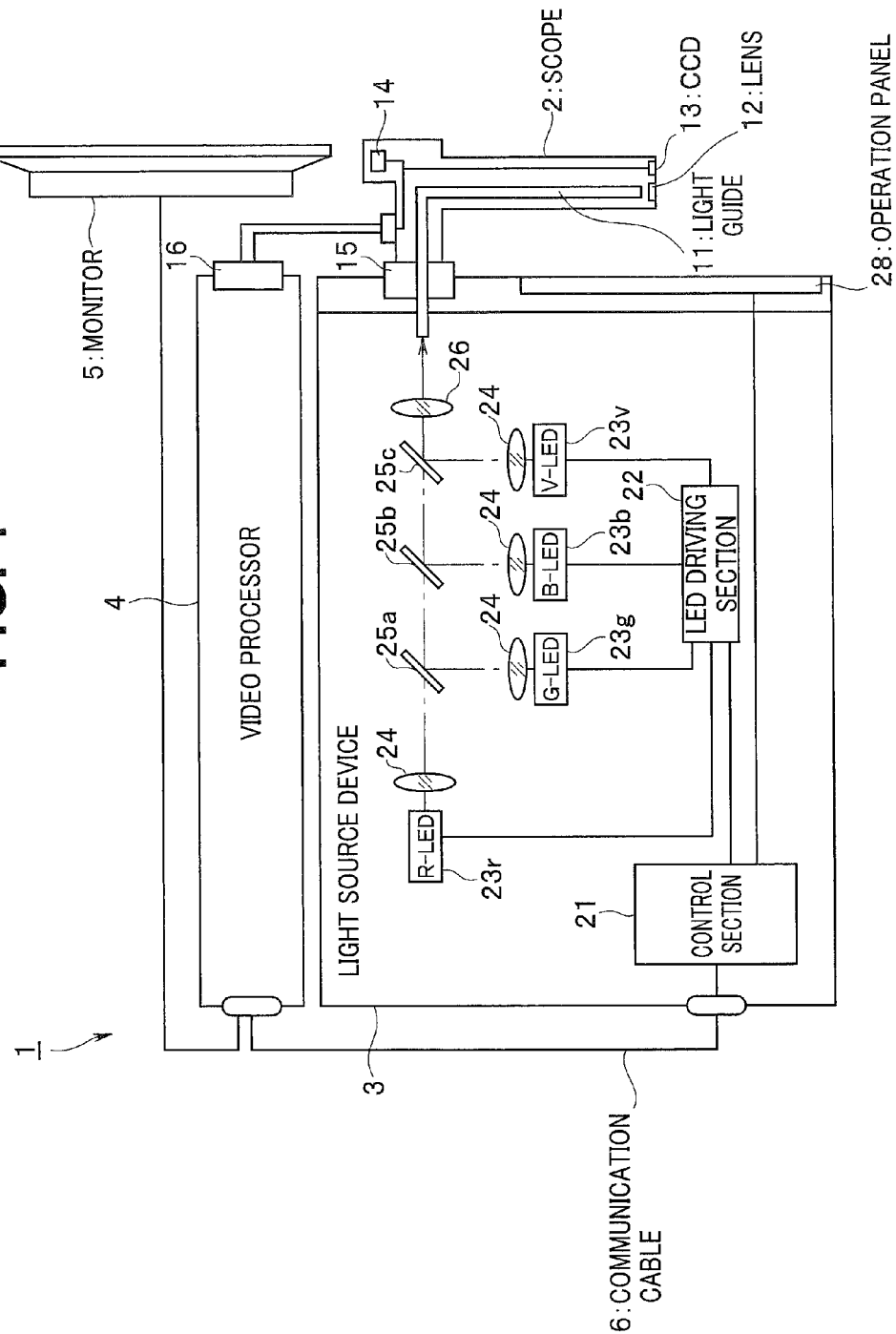
FIG. 1 is a diagram showing a configuration of an endoscope system in a first embodiment of the present invention.

FIG. 1 to FIG. 4 show a first embodiment of the present invention. FIG. 1 is a diagram showing a configuration of an endoscope system.

An endoscope system 1 includes a scope 2, a light source device 3, a video processor 4, a monitor 5, and a communication cable 6.

The light source device 3 includes, as light sources, light emitting elements of a plurality of colors, more specifically, a red LED (R-LED) 23r, which is a red (R) light emitting element, a green LED (G-LED) 23g, which is a green (G) light emitting element, a blue LED (B-LED) 23b, which is a blue (B) light emitting element, and a violet LED (V-LED) 23v, which is a violet (V) light emitting element.

Figure 11:
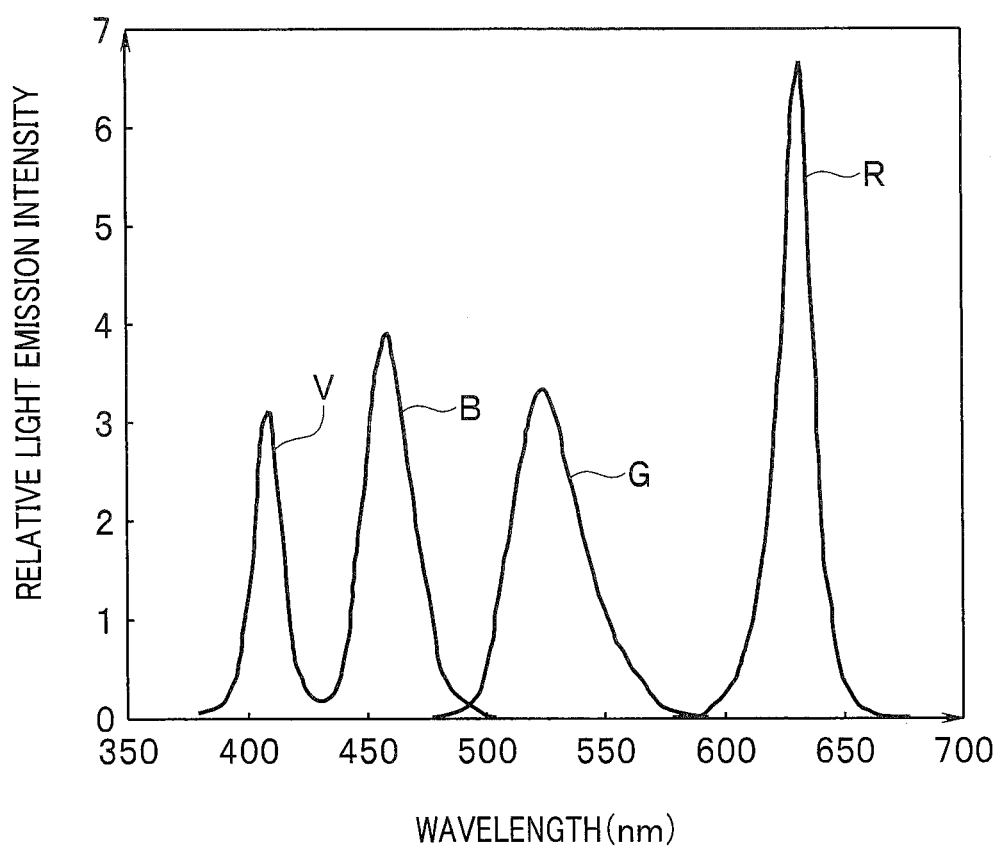
FIG. 11 is a diagram showing spectra at a time when the conventional LED lighting control shown in FIG. 10 is performed.

Lights emitted from these light emitting elements can form white light. In the present embodiment, among respective color bands of red, green, and blue, which are bands of three primary colors forming the white light, light emitted from the red LED 23r forms the red band, light emitted from the green LED 23g forms the green band, and light emitted from the blue LED 23b and narrowband light emitted from the violet LED 23v form the blue band (see FIG. 11 as well).

It is known that, when light having a narrow-banded wavelength easily absorbed by hemoglobin in blood is radiated, a blood vessel is highlighted and observed. The violet LED 23v in the present embodiment is an LED for performing such narrowband light observation (narrow band imaging: NBI (registered trademark)) and emits narrowband light having a wavelength of, for example, 390 to 445 nm. When the narrowband light observation is performed using the violet LED 23v, it is possible to highlight and observe, for example, a capillary of a mucous membrane surface layer. It is known that, if observation by narrowband light having a wavelength of 530 to 550 nm is performed, it is possible to enhance contrast between thick blood vessel observation in a deep part and the capillary of the mucous membrane surface layer. Therefore, the green LED 23g in the present embodiment emits the narrowband light and also functions as a light emitting element for narrowband.

Therefore, the endoscope system 1 in the present embodiment can be set to observation modes including a white light observation mode and a narrowband light observation mode.

An LED driving section 22 provided in the light source device 3 supplies driving currents respectively to the red LED 23r, the green LED 23g, the blue LED 23b, and the violet LED 23v to drive the LEDs.

A control section 21 provided in the light source device 3 controls the LED driving section 22 to adjust light emission intensities and light emission periods of respective emitted lights of the red LED 23r, the green LED 23g, the blue LED 23b, and the violet LED 23v. The control by the control section 21 is performed on the basis of, for example, information concerning an exposure period and a present brightness value of an object acquired by performing communication with the video processor 4 via the communication cable 6.

In the light source device 3, as optical systems for transmitting illumination light, four collimator lenses 24, three dichroic filters 25a, 25b, and 25c, and one condensing lens 26 are provided.

The four collimator lenses 24 are disposed on optical paths of respective emitted lights of the red LED 23r, the green LED 23g, the blue LED 23b, and the violet LED 23v. The four collimator lenses 24 emit incident light as parallel beams.

The first dichroic filter 25a transmits red light R emitted from the red LED 23r and reflects green light G emitted from the green LED 23g.

The second dichroic filter 25b transmits the red light R emitted from the red LED 23r and the green light G emitted from the green LED 23g and reflects blue light B emitted from the blue LED 23b.

The third dichroic filter 25c transmits the red light R emitted from the red LED 23r, the green light G emitted from the green LED 23g, and the blue light B emitted from the blue LED 23b and reflects the narrowband light V having a violet color emitted from the violet LED 23v.

The condensing lens 26 condenses a parallel light beams received from the third dichroic filter 25c on an incident end face of a proximal end of a light guide 11 of the scope 2.

An operation panel 28 provided in the light source device 3 is an operation panel with which the user performs operation for the light source device 3. With the operation panel 28, the user can perform power ON/OFF operation, setting operation for the observation modes such as the white light observation mode and the narrowband light observation mode, and the like. An observation mode inputted from the operation panel 28 is transmitted to the video processor 4 via the control section 21 and the communication cable 6. Image processing corresponding to the observation mode is performed.

The scope 2, which is an endoscope that receives supply of illumination light from such a light source device 3 includes the light guide 11, a lens 12, a CCD 13, a scope-ID storing section 14, a light guide connector 15, and a video connector 16.

A proximal end of the light guide 11 extends from the light guide connector 15. When the light guide connector 15 is connected to the light source device 3, light from the condensing lens 26 is condensed on an incident end face of the proximal end of the light guide 11.

The light guide 11 is inserted through to a distal end portion in an insertion section of the scope 2. The light guide 11 emits illumination light from an emission surface of a distal end. The lens 12 for illumination is disposed on an optical path of the illumination light at the distal end of the scope 2. In this way, the illumination light from the light source device 3 transmitted in the light guide 11 is radiated on the subject from the distal end of the insertion section via the lens 12.

An optical image of the subject, on which the illumination light is radiated, is captured via a not-shown objective lens disposed at the insertion section distal end of the scope 2 and formed on the CCD 13, which is an image pickup device. The CCD 13 is a monochrome image pickup device that receives frame-sequential illumination light (on the other hand, if the light source device 3 is a simultaneous illumination type, the CCD 13 is a color image pickup device on which a color filter array or the like is disposed). The CCD 13 performs image pickup for converting the optical image of the subject into an electric signal and transmits the electric signal to the video processor 4, to which the video connector 16 is connected, via a signal line. Note that the CCD 13 is used as the image pickup device. However, the image pickup device is not limited to this. A CMOS or other image pickup devices may be used.

The scope-ID storing section 14 is a storing section that stores identification information of the scope 2 in a non-volatile manner. In the scope-ID storing section 14, information such as a product number and a manufacturing serial number of the scope 2, time required for readout of the CCD 13, and color balance values indicating light amount ratios required of lights of a plurality of colors are stored. The color balance values are RBG light amount ratios RCr, RCg, and RCb needed in the white light observation mode and GV light amount ratios RNg and RNv needed in the narrowband light observation mode by an image pickup system (the CCD 13, the objective lens, etc.) of the scope 2 (i.e., the color balance values are set for each observation mode and, when there is another observation mode, set for the observation mode). That is, photodiodes configured in pixels of the CCD 13, which is the monochrome image pickup device, have different sensitivities depending on bands of received light. Even if light having the same light amount is received, a generated charge amount is different when the received light is in the red band, when the received light is in the green band, and when the received light is in the blue band. An image displayed on the monitor 5 is observed by human eyes. Therefore, the image needs to have a color balance adjusted to the human eyes. Therefore, the RGB light amount ratios RCr, RCg, and RCb are set to values indicating ratios of light amounts that should be respectively received in the red band, the green band, and the blue band in order to generate electric charges color-balanced (in the white light observation mode, white-balanced) after taking into account such various elements. Similarly, the GV light amount ratios RNg and RNv are set to values indicating ratios of light amounts that should be respectively received in the green narrowband and the violet narrow band in order to generate electric charges color-balanced (color-balanced in green and violet) in the narrowband light observation mode. The information stored in the scope-ID storing section 14 is read out by the video processor 4 via a signal line.

The video processor 4 synchronizes the respective color images received from the CCD 13 to generate a color image signal and, after performing image processing such as color balance adjustment, gamma conversion, and color conversion, converts the color image signal into a signal format for display on the monitor 5 and outputs the color image signal to the monitor 5.

In the white light observation mode, the video processor 4 performs image processing for generating a white light observation image using, for example, a 3×3 matrix of input three components (an R component, a G component, and a (B+V) component) and output three components (an R component, a G component, and a B component).

In the narrowband light observation mode, the video processor 4 performs image processing for generating a narrow band light observation image using, for example, a 3×2 matrix of input two components (a G component and a V component) and output three components (an R component, a G component, and a B component). That is, in the narrowband light observation mode, even if color components obtained from the CCD 13 is two colors, an image displayed on the monitor 5 is a color display image of three colors.

Further, the video processor 4 extracts, for example, a luminance signal from the received respective color images and generates information concerning a present brightness value on the basis of the extracted luminance signal. The information concerning the present brightness value generated by the video processor 4 in this way is transmitted to the control section 21 of the light source device 3 via the communication cable 6 that connects the video processor 4 and the light source device 3.

The control section 21 performs, on the basis of the received information concerning the present brightness value, control of light emission intensities of the respective color LEDs as explained above via the LED driving section 22. The control section 21 acquires the color balance values stored in the scope-ID storing section 14 via the video processor 4 and performs color balance adjustment of the illumination light, that is, in the white light observation mode, balance adjustment of light emission intensities of the red LED 23r, the green LED 23g, the blue LED 23b, and the violet LED 23v and, in the narrowband light observation mode, balance adjustment of light emission intensities of the green LED 23g and the violet LED 23v. As explained above, when an image in the blue band in the white light observation mode is acquired, the control section 21 causes both of the blue LED 23b and the violet LED 23v to emit lights. By adopting such a light emission form, it is possible to give a margin to an emitted light amount in the blue band.

Figure 2:
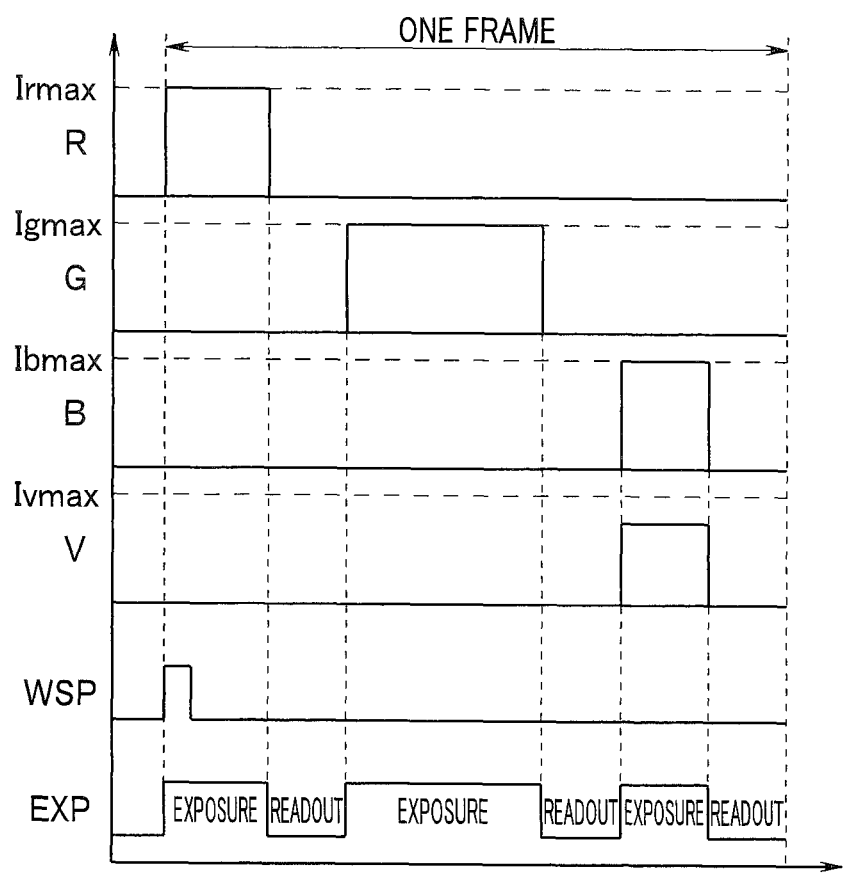
FIG. 2 is a timing chart showing light emission timings of respective color LEDs at a time when frame-sequential lighting of a white light observation mode is performed in the first embodiment.

FIG. 2 is a timing chart showing light emission timings of the respective color LEDs at a time when frame-sequential illumination of the white light observation mode is performed.

The CCD 13 alternately performs an operation in an exposure period in which light is received and electric charges are accumulated and an operation in a readout period in which the accumulated electric charges are sequentially read out for each pixel.

In a case of the frame-sequential illumination, the CCD 13 causes the LED of any one band to emit light and performs exposure in the exposure period and extinguishes all the LEDs and performs readout of an exposed image in the readout period.

That is, when starting exposure of one frame, the video processor 4 outputs a frame start signal WSP (see FIG. 2) to the light source device 3 and outputs an LED lighting control signal EXP (see FIG. 2), which is a light emitting element lighting control signal indicating the exposure periods (i.e., maximum light emission periods of the LEDs), to the light source device 3.

When a rising edge of the frame start signal WSP is detected, the light source device 3 causes, for example, only the red LED 23r to emit light in an exposure period of a first field in one frame in which the LED lighting control signal EXP is high. Consequently, the CCD 13 receives the red light R from the illuminated subject and performs exposure.

When the LED lighting control signal EXP changes to low, the light source device 3 detects that the exposure period of the first field ends and extinguishes all the LEDs. After the exposure period ends, the video processor 4 shifts to the readout period and performs, from the CCD 13, readout of an R image obtained by the exposure with the red light R.

When the readout period of the first field ends, the video processor 4 shifts to an exposure period of a second field and changes the LED lighting control signal EXP to high. The light source device 3 causes, for example, only the green LED 23g to emit light in the exposure period of the second field in which the LED lighting control signal EXP is high. Consequently, the CCD 13 receives the green light G from the illuminated subject and performs exposure.

When the LED lighting control signal EXP changes to low, the light source device 3 detects that the exposure period of the second field ends and extinguishes all the LEDs. After the exposure period ends, the video processor 4 shifts to the readout period and performs, from the CCD 13, readout of a G image obtained by the exposure with the green light G.

When the readout period of the second field ends, the video processor 4 shifts to an exposure period of a third field and changes the LED lighting control signal EXP to high. In the exposure period of the third field in which the LED lighting control signal EXP is high, the light source device 3 causes, for example, only the blue LED 23b and the violet LED 23v to emit lights. Consequently, the CCD 13 receives the blue light B and the narrowband light V from the illuminated subject and performs exposure.

When the LED lighting control signal EXP changes to low, the light source device 3 detects that the exposure period of the third field ends and extinguishes all the LEDs. After the exposure period ends, the video processor 4 shifts to the readout period and performs, from the CCD 13, readout of a BV image obtained by the exposure with the blue light B and the narrowband light V.

In this way, after detecting the rising edge of the frame start signal WSP, the light source device 3 performs light emission in predetermined order, that is, order of R→G→(B+V) according to a period in which the LED lighting control signal EXP is high.

The light source device 3 repeatedly performs the cycle of one frame explained above to acquire images of a plurality of frames.

In the LED lighting control signal EXP outputted to the light source device 3 by the video processor 4, as shown in FIG. 2, all the fields are not the same, that is, one frame is not equally divided into three field periods. Therefore, exposure periods of the respective colors, that is, maximum light emission periods of the respective color LEDs are different for each color. Setting of the maximum light emission periods is performed such that a maximum emitted light amount can be obtained when light emission luminances of the respective color LEDs are maximized (therefore, the maximum emitted light amount of the light source device 3 increases more than when one frame is equally divided into three to form fields).

Figure 3:
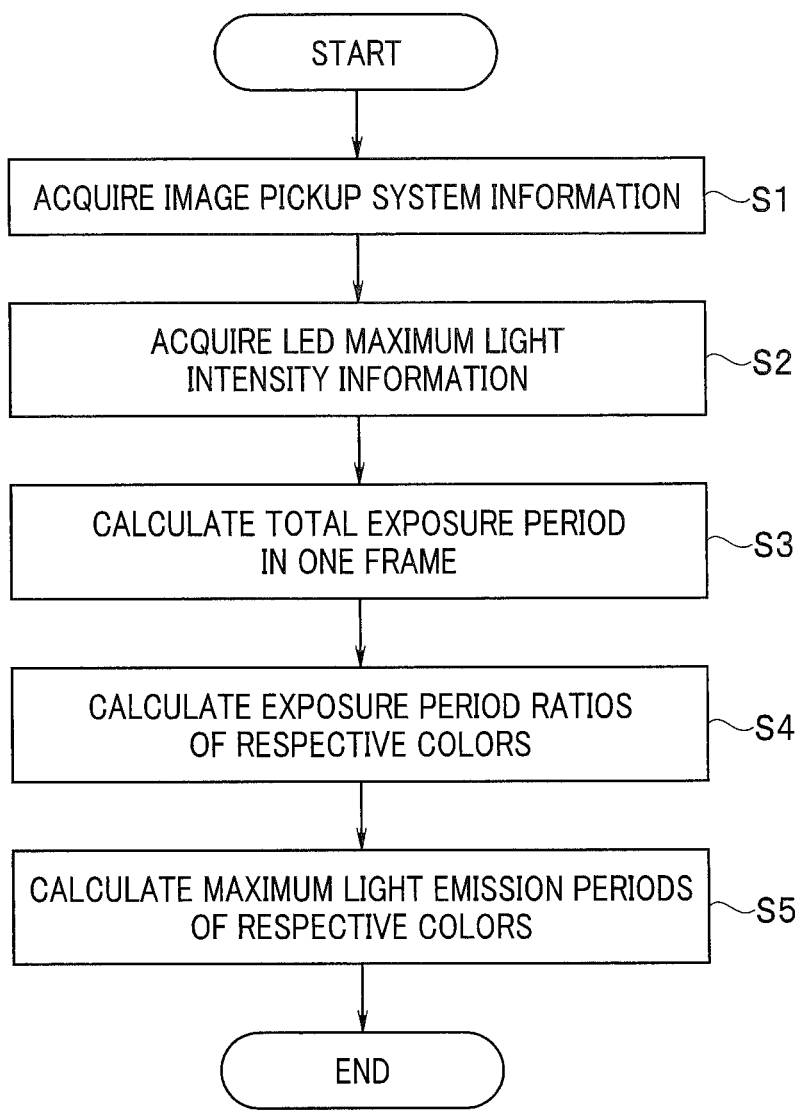
FIG. 3 is a flowchart for explaining setting processing for exposure periods by a video processor in the first embodiment.

The setting of the exposure periods is explained with reference to FIG. 3. FIG. 3 is a flowchart for explaining setting processing for exposure periods by the video processor 4.

When the scope 2 is connected, the video processor 4 acquires type information of the scope 2 from the scope-ID storing section 14 and acquires information concerning the image pickup system, that is, information such as time required for readout of the CCD 13 (a readout period) and the color balance values in the white light observation mode explained above from the scope-ID storing section 14 (step S1).

Further, the video processor 4 performs communication with the light source device 3 and acquires information concerning maximum light emission intensities of the respective color LEDs (light emission intensities at a time when maximum rated currents Irmax, Igmax, Ibmax, and Ivmax are supplied respectively to the respective color LEDs 23r, 23g, 23b, and 23v) (step S2).

Subsequently, the video processor 4 subtracts three fields of a readout period Tf acquired in step S1 from one frame cycle TF and calculates a total exposure period Texp in one frame as indicated by the following Equation 1 (step S3).

$$Texp = TF - 3 \times Tf \qquad \text{[Equation 1]}$$

The video processor 4 calculates ratios kr, kg, and kb of the exposure periods of the respective colors as indicated by the following Equation 2 on the basis of the RGB light amount ratios RCr, RCg, and RCb, which are the color balance values, acquired in step S1 and the maximum light emission intensity Lr of a red light emitting element section (the red LED 23r), the maximum light emission intensity Lg of a green light emitting element section (the green LED 23g), and maximum light emission intensity Lbv of a blue light emitting element section (a combination of the blue LED 23b and the violet LED 23v) (step S4).

$$kr : kg : kb = (RCr/Lr) : (RCg/Lg) : (RCb/Lbv) \qquad \text{[Equation 2]}$$

Note that, in the present embodiment, a ratio of the light emission intensities of the violet LED 23v and the blue LED 23b is fixed (a fixed ratio for satisfying light intensity of B>light intensity of V). (The light emission intensity of the blue LED 23b)+(the light emission intensity of the violet LED 23v) at a time when the blue LED 23b reaches the maximum rated current is set as a maximum light emission intensity Lbv of the blue light emitting element section. Therefore, in the white light observation mode, it only has to be considered that the violet LED 23v and the blue LED 23b configure one group of light emitting elements that emit lights in the blue band.

Thereafter, the video processor 4 calculates, as indicated by the following Equation 3, a maximum light emission period Tr of the red light emitting element section (the red LED 23r), a maximum light emission period Tg of the green light emitting element section (the green LED 23g), and a maximum exposure period Tb of the blue light emitting element section (a combination of the blue LED 23b and the violet LED 23v) corresponding to the exposure periods of the respective colors (step S5) and ends the processing.

$$Tr = \{kr/(kr+kg+kb)\} \times Texp$$

$$Tg = \{kg/(kr+kg+kb)\} \times Texp$$

$$Tb = \{kb/(kr+kg+kb)\} \times Texp \qquad \text{[Equation 3]}$$

FIG. 2 shows waveforms at a time when, in the maximum light emission periods Tr, Tg, and Tb of the respective color LEDs set in this way, the respective color LEDs are caused to emit lights with maximum light emission intensities in order to obtain maximum emitted light amounts, that is, the respective maximum rated currents Irmax, Igmax, Ibmax, and Ivmax are supplied to the respective color LEDs 23r, 23g, 23b, and 23v.

That is, the respective color LEDs emit lights at the maximum light emission intensities in all the exposure periods (all the periods in which lights can be emitted excluding the readout periods) and the frame-sequential illumination light is in a color-balanced state. Therefore, light emission abilities of the respective color LEDs can be utilized to maximum.

Figure 4:
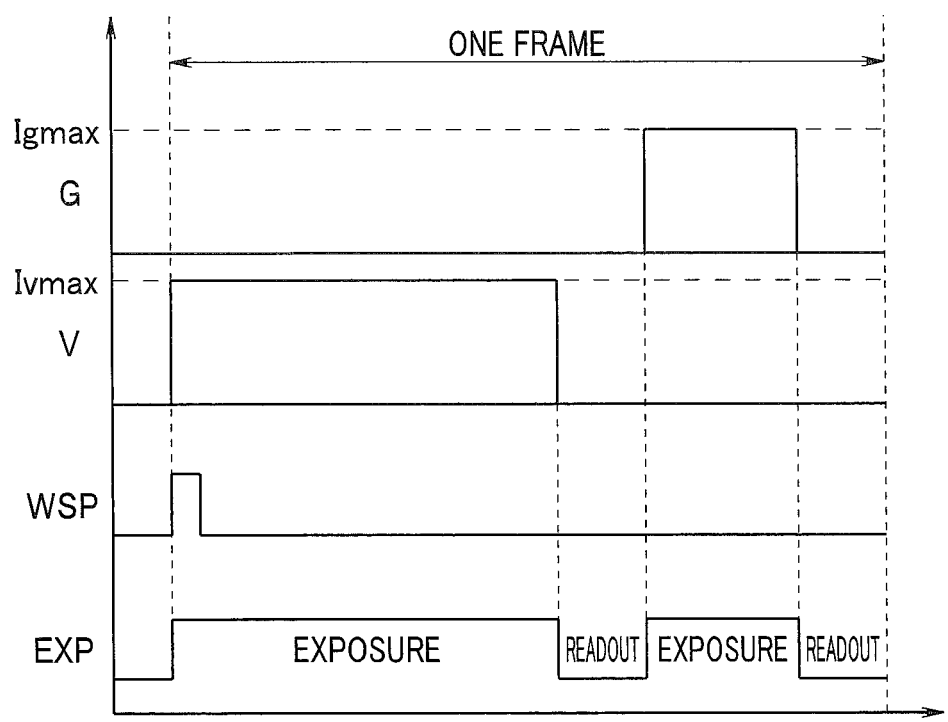
FIG. 4 is a timing chart showing light emission timings of the respective color LEDs at a time when frame-sequential lighting of a narrowband light observation mode is performed in the first embodiment.

FIG. 4 is a timing chart for explaining light emission timings of the respective color LEDs at a time of the frame-sequential illumination of the narrowband light observation mode is performed.

In the narrow band light observation mode as well, when starting exposure of one frame, the video processor 4 outputs the frame start signal WSP (see FIG. 4) to the light source device 3 and outputs the LED lighting control signal EXP (see FIG. 4), which is the light emitting element lighting control signal indicating the exposure period, to the light source device 3.

When a rising edge of the frame start signal WSP is detected, the light source device 3 causes, for example, only the violet LED 23v to emit light in the exposure period of the first field in one frame in which the LED lighting control signal EXP is high. Consequently, the CCD 13 receives the narrowband light V from the illuminated subject and performs exposure.

When the LED lighting control signal EXP changes to low, the light source device 3 detects that the exposure period of the first field ends and extinguishes all the LEDs. After the exposure period ends, the video processor 4 shifts to the readout period and performs, from the CCD 13, readout of a V image obtained by the exposure with the narrowband light V.

When the readout period of the first field ends, the video processor 4 shifts to the exposure period of the second field and changes the LED lighting control signal EXP to high. The light source device 3 causes, for example, only the green LED 23g to emit light in the exposure period of the second field in which the LED lighting control signal EXP is high. Consequently, the CCD 13 receives the green light G from the illuminated subject and performs exposure.

When the LED lighting control signal EXP changes to low, the light source device 3 detects that the exposure period of the second field ends and extinguishes all the LEDs. After the exposure period ends, the video processor 4 shifts to the readout period and performs, from the CCD 13, readout of a G image obtained by the exposure with the green light G.

In this way, after detecting the rising edge of the frame start signal WSP, the light source device 3 performs light emission in predetermined order, that is, order of V→G according to a period in which the LED lighting control signal EXP is high.

The light source device 3 repeatedly performs the cycle of one frame explained above to acquire images of a plurality of frames in the narrowband light observation mode.

A method of setting the exposure periods for obtaining the maximum emitted light amounts in the narrowband light observation mode is substantially the same as the method in the white light observation mode and is performed by the processing similar to the processing shown in FIG. 3.

That is, when being set in the narrowband light observation mode, the video processor 4 acquires, from the scope-ID storing section 14, information concerning the image pickup system, that is, information such as time required for readout of the CCD 13 (a readout period) and the color balance values in the narrowband light observation mode explained above (step S1).

Further, the video processor 4 performs communication with the light source device 3 and acquires information concerning maximum light emission intensities Lg and Lv of the green LED 23g and the violet LED 23v used in the narrowband light observation (step S2).

Subsequently, the video processor 4 subtracts two fields of the readout period Tf acquired in step S1 from one frame cycle TNF in the narrowband light observation mode and calculates a total exposure period TNexp in one frame in the narrowband light observation mode as indicated by the following Equation 4 (step S3).

$$TNexp = TNF - 2 \times Tf \quad \text{[Equation 4]}$$

The video processor 4 calculates ratios kNg and kNv of the exposure periods of the respective narrow bands as indicated by the following Equation 5 on the basis of the GV light amount ratios RNg and RNv, which are the color balance values, acquired in step S1 and the maximum light emission intensity Lg of the green LED 23g and the maximum light emission intensity Lv of the violet LED 23v acquired in step S2 (step S4).

$$kNg:kNv = (RNg/Lg):(RNb/Lv) \quad \text{[Equation 5]}$$

Thereafter, the video processor 4 calculates, as indicated by the following Equation 6, a maximum light emission period TNg of the green LED 23g and a maximum light emission period TNv of the violet LED 23v corresponding to the exposure periods of the respective colors in the narrowband light observation mode (step S5) and ends the processing.

$$TNg = \{kNg/(kNg+kNv)\} \times TNexp$$

$$TNv = \{kNv/(kNg+kNv)\} \times TNexp \quad \text{[Equation 6]}$$

FIG. 4 shows waveforms at a time when, in the maximum light emission periods TNg and TNv of the green/violet LEDs in the narrowband light observation mode set in this way, the green/violet LEDs are caused to emit lights with the maximum light emission intensities in order to obtain the maximum emitted light amounts, that is, the respective maximum rated currents Igmax and Ivmax are supplied to the green/violet LEDs 23g and 23v. In the narrowband light observation mode, since violet needs a larger light amount, in the example shown in FIG. 4, the exposure period of violet is set longer than the exposure period of green.

Note that, in FIG. 2 and FIG. 4, the waveforms of the driving currents supplied to the respective color LEDs when the illumination light is set to the maximum light amount are shown. However, during actual operation, the light source device 3 performs automatic light adjustment on the basis of information concerning a present brightness value inputted from the video processor 4.

In the automatic light adjustment, the respective color LEDs only have to be subjected to pulse width modulation (PWM) control in the maximum light emission periods of the respective colors, or the driving currents supplied to the respective color LEDs only have to be controlled, or these kinds of control only have to be combined.

Note that when the automatic light adjustment is performed by the pulse width modulation control in the maximum light emission periods, in order to improve a frame rate, the light source device 3 may transmit end timings of the light emission periods of the respective color LEDs to the video processor 4.

That is, the video processor 4 notifies the light source device 3 of start timings of the exposure periods of the respective fields. The light source device 3 receives the notification and causes the LED of any one of the colors corresponding to a field to emit light. When an emitted light amount at a present point (the emitted light amount only has to be calculated by integrating, with time, for example, light emission intensities associated with driving currents or only have to be calculated by integrating, with time, sensor values of illuminance sensors or the like provided respectively corresponding to the respective color LEDs) reaches a calculated emitted light amount, the light source device 3 notifies the video processor 4 of end timing of the light emission period.

Upon receiving the end timing of the light emission period, the video processor 4 immediately shifts to the readout period without waiting for an end of the exposure period during the maximum light amount. When the readout period ends, the video processor 4 notifies the light source device 3 of start timings of the exposure period of the next field in the same manner as explained above.

By repeatedly performing such processing, it is possible to improve the frame rate. For example, during near point observation, since a distance from the insertion section distal end of the scope 2 to the subject is short, a light amount of the illumination light may also be small. Therefore, there is an advantage that the improvement of the frame rate in such a case can be attained.

Note that, in the above explanation, the CCD 13, which is the image pickup device, is disposed at the insertion section distal end portion of the scope 2. However, without being limited thereto, the configuration may be one in which an optical image is transmitted via a relay optical system or the like and image pickup is performed on a hand side of the scope 2 or in the video processor. Therefore, the image pickup device is not always included in the endoscope.

Figure 10:
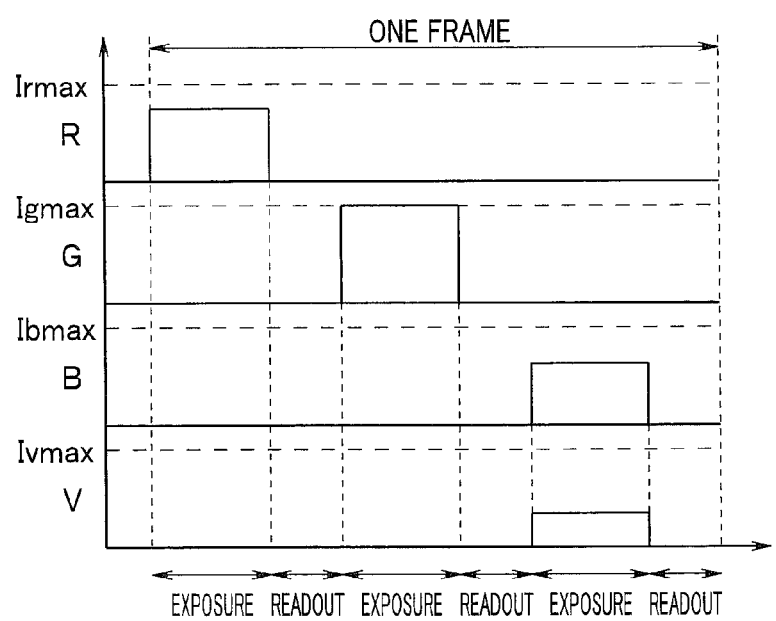
FIG. 10 is a timing chart of conventional LED lighting control at a time when normal observation is performed with a maximum light amount.

With the endoscope system and the operation method for the endoscope system in the first embodiment, in the illumination of the frame-sequential type performed using the light emitting elements of the plurality of colors, it is possible to further increase the maximum emitted light amounts than a conventional driving method shown in FIG. 10.

Moreover, when the light emission intensities are maximized, in the color-balanced state, light emission is performed at the maximum light emission intensities in all the periods in which the light emitting elements of the respective colors can emit lights. Therefore, it is possible to utilize light emitting abilities of the light emitting elements of the respective colors to maximum. Consequently, it is possible to solve a light amount shortage of the green light at a time when the LEDs are used as the light sources and bring the light amount close to a light amount at a time when a xenon lamp is used as the light source.

When the automatic light adjustment is performed by the pulse width modulation control in the maximum light emission periods, if the light source device 3 notifies the video processor 4 of the end timing of the light emission period, it is possible to improve the frame rate.

[Second Embodiment]

Figure 5:
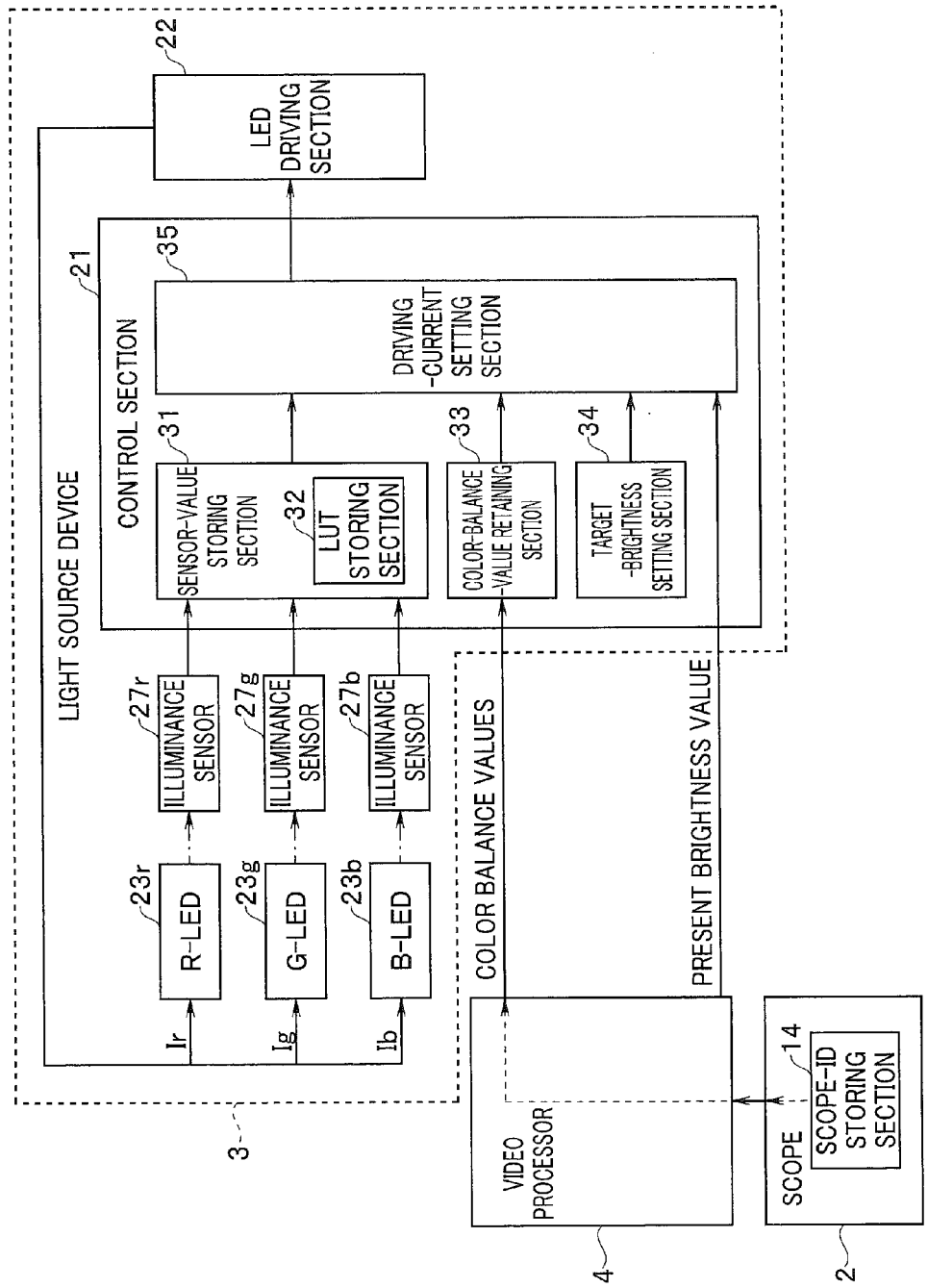
FIG. 5 is a block diagram showing a configuration of an endoscope system in a second embodiment of the present invention.
Figure 7:
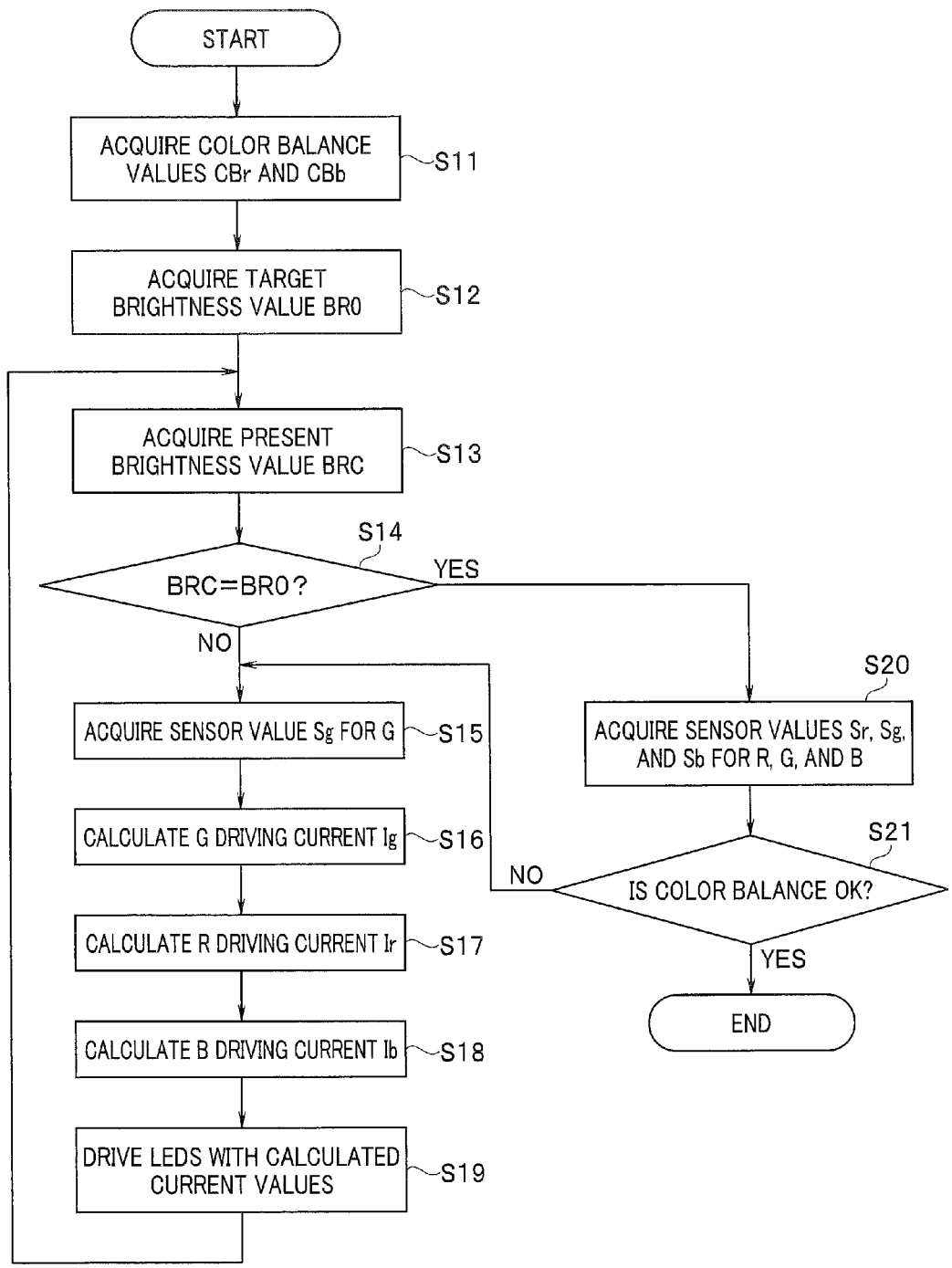
FIG. 7 is a flowchart showing processing of automatic light adjustment in which a color balance is maintained in the second embodiment.

FIG. 5 to FIG. 7 show a second embodiment of the present invention. FIG. 5 is a block diagram showing a configuration of an endoscope system.

In the second embodiment, portions same as the portions in the first embodiment are denoted by the same reference numerals and signs and explanation of the portions is omitted. Only differences from the first embodiment are mainly explained.

Note that, in the present embodiment, to simplify explanation, illustration and explanation of the violet LED 23v and components related to the violet LED 23v are omitted. However, even when the violet LED 23v is provided, the following explanation can be applied the same way.

In the present embodiment, the automatic light adjustment is performed by controlling the driving currents supplied to the respective color LEDs in the maximum light emission periods as explained above.

That is, in the light source device 3 in the present embodiment, as shown in FIG. 5, as light-intensity detecting sections that detect light emission intensities of light emitting elements of a plurality of colors, an illuminance sensor 27r that detects light emission intensity of the red LED 23r, an illuminance sensor 27g that detects light emission intensity of the green LED 23g, and an illuminance sensor 27b that detects light emission intensity of the blue LED 23b are provided. The illuminance sensors 27r, 27g, and 27b are disposed in positions (e.g., in vicinities of the respective color LEDs 23r, 23g, and 23b) where leak light not reaching the incident end face of the light guide 11 within light beams emitted from the respective color LEDs 23r, 23g, and 23b is detected. The illuminance sensor 27r, 27g, and 27b output results of the detection of the light intensities to the control section 21.

The control section 21 includes a sensor-value storing section 31 including an LUT storing section 32, a color-balance-value retaining section 33, a target-brightness setting section 34, and a driving-current setting section 35.

The sensor-value storing section 31 stores sensor values of results detected by the respective illuminance sensors 27r, 27g, and 27g.

The LUT storing section 32 is a lookup-table storing section that stores, as a lookup table (LUT), sensor values obtained from the respective illuminance sensors 27r, 27g, and 27b by respectively gradually changing the driving currents Ir, Ig, and Ib of the respective color LEDs 23r, 23g, and 23b from minimum rated currents to maximum rated currents. The lookup table is not limited to retention of data stored during manufacturing. The lookup table may be updated at appropriate update timing, for example, when a power supply of the endoscope system 1 (more limitedly, the light source device 3) is turned on or color balance values set in the color-balance-value retaining section 33 are changed. In this case, the LUT storing section 32 is configured as a rewritable storing section. Consequently, it is possible to improve a color balance and accuracy of light adjustment at any point in time. FIG. 6 is a diagram showing an example of the lookup table stored in the LUT storing section 32. Note that what are described in the lookup table are, among the described items in FIG. 6, concerning columns, respective columns Ig, Sg, Ir, Sr, Ib, and Sb, concerning rows, respective rows excluding rows of Ib=10.83 and Ir=13.33, and other fields are descriptions added as references for the explanation.

The color-balance-value retaining section 33 stores and retains color balance values read out from the scope-ID storing section 14 by the video processor 4.

The target-brightness setting section 34 retains a brightness value set as a target that information concerning a present brightness value generated and outputted by the video processor 4 should reach.

The driving-current setting section 35 performs automatic light adjustment for setting driving currents of the light emitting elements of the plurality of colors on the basis of the color balance values read out from the color-balance-value retaining section 33, the target brightness value read out from the target-brightness setting section 34, the present brightness value received from the video processor 4, and a reference result of the lookup table stored in the LUT storing section 32 of the sensor-value storing section 31 such that the present brightness value reaches the target brightness value and light amount ratios of the lights of the plurality of colors are light amount ratios indicated by the color balance values.

The automatic light adjustment in which a color balance is maintained in the present embodiment is explained with reference to FIG. 5 to FIG. 7. FIG. 7 is a flowchart for explaining processing of the automatic light adjustment in which the color balance is maintained.

When the processing shown in FIG. 7 is started, the light source device 3 acquires the color balance values from the scope-ID storing section 14 via the video processor 4 and causes the color-balance-value retaining section 33 to store the color balance values. It is assumed that the color balance values stored by the color-balance-value retaining section 33 are a light amount CBr of red light and a light amount CBb of blue light at a time when a light amount of green light is standardized as 1. If the RGB light amount ratios RCr, RCg, and RCb explained in the first embodiment are used, CBr=RCr/RCg and CBb=RCb/RCg. In the example shown in FIG. 6, CBr=0.8 and CBb=1.3.

The driving-current setting section 35 acquires CBr and CBb as the color balance values from the color-balance-value retaining section 33 (step S11).

Subsequently, the driving-current setting section 35 acquires a target brightness value BR0 from the target-brightness setting section 34 (step S12).

Further, the driving-current setting section 35 acquires a present brightness value BRC from the video processor 4 (step S13).

The driving-current setting section 35 determines whether the target brightness value BR0 and the present brightness value BRC are equal (step S14).

When it is determined that the target brightness value BR0 and the present brightness value BRC are not equal, the driving-current setting section 35 acquires a present sensor value Sg of the illuminance sensor 27g for G via the sensor-value storing section 31 (step S15). The driving-current setting section 35 calculates, referring to the lookup table in the LUT storing section 32, a driving current Ig to be supplied to the green LED 23g with which a sensor value of Sg×(BR0/BRC) is obtained (step S16).

For example, it is assumed that the calculated driving current Ig is 10 (see FIG. 6).

Subsequently, the driving-current setting section 35 multiplies the sensor value Sg=100 corresponding to the calculated driving current Ig=10 with the color balance value CBr=0.8 as shown in a fourth column of FIG. 6 and calculates a sensor value Sr of the illuminance sensor 27r for R with which a color balance is obtained with respect to Sg=100. Here, the sensor value Sr is 80. Further, the driving-current setting section 35 calculates, referring to the lookup table in the LUT storing section 32, a driving current Ir to be supplied to the red LED 23r with which Sr=80 (step S17). In the example shown in FIG. 6, since a field corresponding to Sr=80 is absent in the lookup table, the driving-current setting section 35 refers to a field of Sr=78 and a field of Sr=84 before and after Sr=80 and interpolates (e.g., linearly interpolates) a result of the reference to thereby obtain a result of Ir=13.33.

Subsequently, the driving-current setting section 35 multiplies the sensor value Sg=100 with the color balance value CBb=1.3 as shown in a seventh column of FIG. 6 and calculates a sensor value Sb of the illuminance sensor 27b for B with which a color balance is obtained with respect to Sg=100. The sensor value Sb is 130. Further the driving-current setting section 35 calculates, referring to the lookup table in the LUT storing section 32, a driving current Ib to be supplied to the blue LED 23b with which Sb=130 (step S18). In the example shown in FIG. 6, since a field corresponding to Sb=130 is absent in the lookup table, the driving-current setting section 35 refers to a field of Sb=120 and a field of Sb=132 before and after Sb=130 and interpolates a result of the reference to thereby obtain a result of Ib=10.83.

In this way, in the present embodiment, the driving currents supplied to the respective color LEDs are calculated with reference to Ig and Sg related to the green LED 23g.

More specifically, the driving current Ir supplied to the red LED 23r is calculated as an electric current with which a sensor value satisfying Sr=CBr×Sg is obtained. The driving current Ib supplied to the blue LED 23b is calculated as an electric current with which a sensor value satisfying Sb=CBb×Sg is obtained.

The respective driving currents Ig, Ir, and Ib obtained in steps S16 to S18 are respectively supplied to the respective color LEDs 23r, 23g, and 23b to cause the color LEDs 23r, 23g, and 23b to emit lights (step S19).

Returning to step S13 explained above, the driving-current setting section 35 acquires the present brightness value BRC based on new driving currents and repeatedly performs the processing explained above.

When it is determined in step S14 that the target brightness value BR0 and the present brightness value BRC are equal, the driving-current setting section 35 acquires the present sensor values Sr, Sg, and Sb of the respective illuminance sensors 27r, 27g, and 27b via the sensor-value storing section 31 (step S20) and determines whether a color balance is a demanded balance (step S21).

When the color balance is not the demanded color balance yet, returning to step S15, the driving-current setting section 35 repeatedly performs the processing explained above.

On the other hand, when the color balance is the demanded color balance, light adjustment in which the color balance is maintained has been performed. Therefore, the driving-current setting section 35 ends the processing.

According to the second embodiment explained above, effects substantially the same as the effects in the first embodiment are attained. The color balance is maintained not only when the color LEDs are caused to emit lights with maximum light amounts but also during light adjustment in which light amounts are changed as appropriate.

The driving currents to the respective color LEDs during the light adjustment are calculated with reference to the lookup table. Therefore, it is possible to improve responsiveness.

The driving currents supplied to the other light emitting elements are calculated with reference to the light emitting element with the lowest light emission efficiency (i.e., the green LED 23g). Therefore, it is possible to prevent a situation in which a light amount of the light emitting element with the lowest light emission efficiency is short and a color balance cannot be kept.

When the lookup table is updated at appropriate update timing, even when the driving currents of the respective color LEDs change or variation occurs in the light emission wavelengths and the light emission intensities of the respective color LEDs because of aged deterioration, it is possible to perform appropriate correction according to a latest state.

[Third Embodiment]

Figure 8:
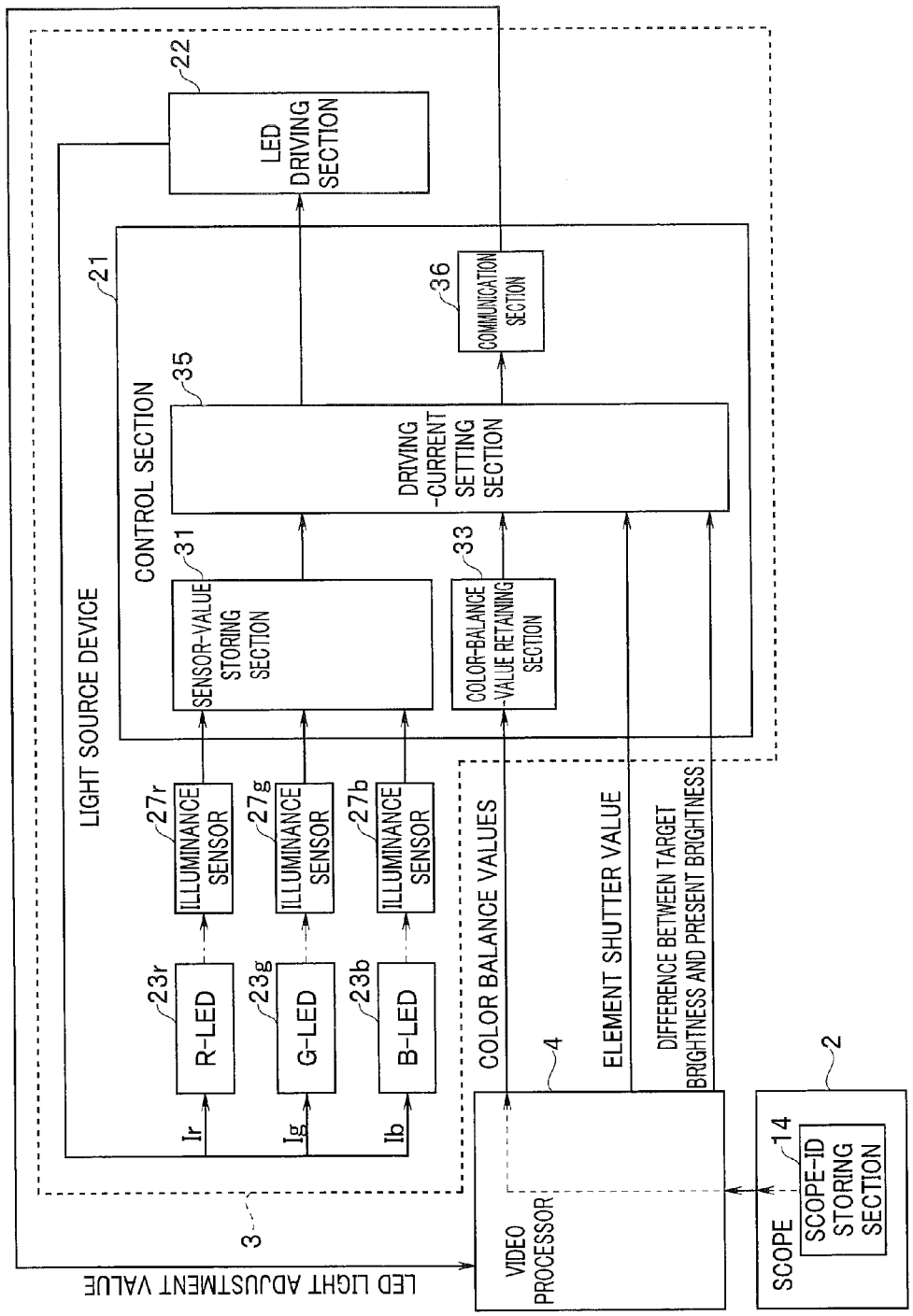
FIG. 8 is a block diagram showing a configuration of an endoscope system in a third embodiment of the present invention.
Figure 9:
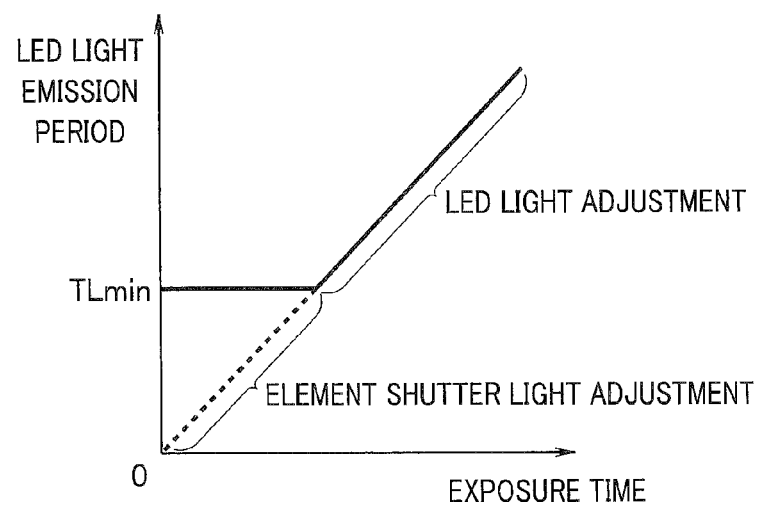
FIG. 9 is a diagram showing an example for distinguishing, according to exposure times, whether light adjustment is performed by control of light emission periods of LEDs or performed by an element shutter.

FIG. 8 and FIG. 9 show a third embodiment of the present invention. FIG. 8 is a block diagram showing a configuration of an endoscope system.

In the third embodiment, portions same as the portions in the first and second embodiments explained above are denoted by the same reference numerals and signs and explanation of the portions is omitted. Only differences from the first and second embodiments are mainly explained.

In the second embodiment explained above, the automatic light adjustment is performed by controlling the driving currents supplied to the respective color LEDs. However, in the present embodiment, the automatic light adjustment is performed by adjusting light emission periods of the respective color LEDs through pulse width modulation in maximum light emission periods. Further, control of exposure times is performed concurrently using an element shutter according to necessary (note that, in the present embodiment, since the element shutter is concurrently used, a total time of exposure periods other than readout periods is not always used for exposure of the CCD 13. Therefore, in the present embodiment, times in which exposure is actually performed in the "exposure periods" are represented as "exposure times").

Therefore, a configuration of the light source device 3 in the present embodiment is substantially the same as the configuration shown in FIG. 5 in the second embodiment explained above. However, the LUT storing section 32 is not provided in the sensor-value storing section 31 (however, when light adjustment is performed on the basis of both of the light emission periods and the driving currents of the LEDs, naturally, the LUT storing section 32 may be provided).

In the second embodiment explained above, the light source device 3 retains the target brightness value. The present brightness value is transmitted from the video processor 4 to the light source device 3. However, in the present embodiment, a difference between the target brightness value and the present brightness value is transmitted from the video processor 4 to the driving-current setting section 35 of the light source device 3. Therefore, the target-brightness setting section 34 is not provided in the light source device 3 in the second embodiment.

Further, in the present embodiment, an element shutter value is transmitted from the video processor 4 to the driving-current setting section 35 of the light source device 3.

A communication section for performing communication with the video processor 4 is provided in the light source devices in the respective embodiments explained above. However, the communication section is not clearly shown in the drawings. On the other hand, in the present embodiment, it is clearly mentioned that a communication section 36 is provided in the light source device 3, the communication section 36 is connected to the driving-current setting section 35, and an LED light adjustment value is outputted from the communication section 36 to the video processor 4.

The CCD 13 of the scope 2 is an image pickup device capable of driving the element shutter.

FIG. 9 is a diagram showing an example for distinguishing, according to exposure times, whether light adjustment is performed by control of light emission periods of LEDs or performed by an element shutter.

The control of the light emission periods of the LEDs is performed by control of continuous application times of the driving currents supplied to the respective color LEDs in the maximum light emission periods shown in FIG. 2, that is, pulse width modulation (PWM) control. However, the control of the light emission periods of the LEDs by the pulse width modulation includes not only limitation of the maximum light emission periods but also limitation of minimum light emission periods (TLmin shown in FIG. 9). It is inappropriate to cause the LEDs to emit lights and perform the light adjustment for time shorter than the minimum light emission period TLmin.

Therefore, when the exposure times are the minimum light emission period TLmin or more, the light adjustment is controlled by performing the pulse width modulation. However, when the exposure times are less than the minimum light emission time TLmin, exposure corresponding to emitted light amounts of light emission periods shorter than the minimum light emission period TLmin is performed while maintaining the light emission periods of the LEDs at, for example, the minimum light emission period TLmin and by concurrently using the element shutter of the CCD 13 based on the control by the video processor 4. As it is widely known, the element shutter is control for setting, as a point in time when the element shutter opens, a point in time of start of exposure to a photodiode (e.g., a point in time when new charges start to be accumulated in the photodiode because charges are transferred from the photodiode to a vertical transfer path (in a case of a CCD) or new charges start to be accumulated in the photodiode because application of a reset voltage to the photodiode ends (in a case of a CMOS)) and setting, as a point in time when the element shutter is closed, a point in time of an end of the exposure to the photodiode (e.g., a point in time when charges are transferred from the photodiode to the vertical transfer path (in the case of the CCD) or a point in time when charges are transferred from the photodiode to a capacitor or a memory such as a floating diffusion (in the case of the CMOS)).

Note that, when the exposure times are less than the minimum light emission time TLmin, it is conceivable that, for example, an exposure start is performed according to a light emission start of the LEDs (i.e., an application start of driving currents to the LEDs) and an exposure end is performed at timing for closing the element shutter. In this case, since the control of the element shutter is performed by the video processor 4, the video processor 4 can immediately shift to the readout periods. It is possible to easily attain improvement of a frame rate. However, the exposure start and the exposure end are not limited to this. It is also possible to, for example, perform the exposure start according to timing when the element shutter is opened after the light emission of the LEDs is started and perform the exposure end at timing for closing the element shutter before the LEDs end the light emission.

Therefore, the driving-current setting section 35 and the video processor 4 of the light source device 3 perform, for each color of the LEDs, for example, control explained below.

The driving-current setting section 35 receives a difference between a target brightness value and a present brightness value from the video processor 4. If the received difference is in a range in which the LED light adjustment can cope with the difference, the driving-current setting section 35 performs LED light adjustment indicated by a solid line in FIG. 9 and transmits a value of the LED light adjustment to the video processor 4. In this case, the video processor 4 does not need to perform the light adjustment by the element shutter.

On the other hand, if the difference between the target brightness value and the present brightness value received from the video processor 4 exceeds the range in which the LED light adjustment can cope with the difference (i.e., the exposure times are less than the minimum light emission period TLmin), the driving-current setting section 35 sets light emission periods of the LEDs to the minimum light emission period TLmin and transmits light adjustment values of the LEDs to the video processor 4.

Upon receiving the LED light adjustment value related to the minimum light emission period TLmin from the light source device 3, the video processor 4 determines whether the difference between the target brightness value and the present brightness value is still present. When determining that the difference is still present even in the minimum light emission period TLmin, the video processor 4 calculates time equivalent to a difference value of the difference and controls, by concurrently using the element shutter, the present brightness value to coincide with the target brightness value.

With such processing, only the LED light adjustment or the light adjustment performed concurrently using the element shutter is executed according to length of the exposure times.

According to the third embodiment explained above, effects substantially the same as the effects in the first and second embodiments explained above are attained. Further, since the element shutter of the image pickup device can perform control with high time resolution, when it is desired to perform exposure same as light emission in time shorter than the minimum light emission period TLmin, it is possible to perform more accurate light adjustment by concurrently using the element shutter.

The light source device 3 receives the difference between the target brightness value and the present brightness value from the video processor 4. Therefore, the light source device 3 does not need to perform comparison or the like and only has to control an LED light adjustment amount according to a value of the received difference. Therefore, it is possible to attain improvement of responsiveness.

Note that the endoscope system including the light source device is mainly explained above. However, the present invention may be an operation method for operating the endoscope system including the light source device as explained above or may be a control program for a computer to control the endoscope system including the light source device as explained above, a computer-readable nontransitory recording medium that records the control program, and the like.

The present invention is not limited to the embodiments per se. In an implementation stage, the constituent elements can be modified and embodied in a range not departing from the spirit of the present invention. Aspects of various inventions can be formed by appropriate combinations of the plurality of constituent elements disclosed in the embodiments. For example, several constituent elements can be deleted from all the constituent elements described in the embodiments. Further, the constituent elements described in different embodiments may be combined as appropriate. In this way, it goes without saying that various modifications and applications are possible in a range not departing from the spirit of the invention.

What is claimed is:

1. An endoscope system comprising:
a plurality of light emitting elements, wherein each of the plurality of light emitting elements is configured to be driven to emit light of a different color at a respective maximum light emission intensity; and
a controller configured to control driving the each of the plurality of light emitting elements to sequentially emit the light of the different color at the respective maximum light emission intensity and at a respective variable exposure period within a frame period; and
a processor comprising hardware, wherein the processor is configured to:
acquire a first ratio of color balance values of each of the different color set for an image sensor configured to capture an optical image based on received light;
acquire a maximum light emission intensity of the each of the plurality of light emitting elements configured to emit the each of the different color;
determine a total exposure period based on a sum of the respective exposure period of the each of the plurality of light emitting elements;
determine a second ratio of the respective exposure period of the each of the plurality of light emitting elements by dividing: (i) the first ratio of color balance values of the each of the different color set for the image sensor by (ii) the maximum light emission intensity of the each of the plurality of light emitting elements configured to emit the each of the different color; and
determine a length of the respective exposure period of the each of the plurality of light emitting elements based on the second ratio of the respective exposure period of the each of the plurality of light emitting elements and the total exposure period.

2. The endoscope system according to claim 1, further comprising:
an endoscope comprising:
optical elements configured to guide and radiate the each of the light of the different color emitted by the each of the plurality of light emitting elements; and
the image sensor.

3. The endoscope system according to claim 2,
wherein the endoscope further comprises a memory configured to store the color balance values, and
wherein the processor is configured to read the color balance values from the memory to acquire the first ratio of the color balance values.

* * * * *